United States Patent
Ma et al.

(10) Patent No.: US 11,337,968 B2
(45) Date of Patent: May 24, 2022

(54) PHENYLQUINOLINE COMPOSITIONS FOR TREATMENT OF OCULAR DISORDERS AND CONDITIONS

(71) Applicant: The Board of Regents of the University of Oklahoma, Norman, OK (US)

(72) Inventors: Jian-xing Ma, Edmond, OK (US); Elizabeth Moran, Boston, MA (US); Guotao Deng, Oklahoma City, OK (US); Adam S. Duerfeldt, Norman, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 474 days.

(21) Appl. No.: 16/097,353

(22) PCT Filed: Apr. 28, 2017

(86) PCT No.: PCT/US2017/030053
§ 371 (c)(1),
(2) Date: Oct. 29, 2018

(87) PCT Pub. No.: WO2017/189958
PCT Pub. Date: Nov. 2, 2017

(65) Prior Publication Data
US 2019/0336491 A1    Nov. 7, 2019

Related U.S. Application Data

(60) Provisional application No. 62/329,543, filed on Apr. 29, 2016.

(51) Int. Cl.
*A61K 31/47* (2006.01)
*A61K 9/00* (2006.01)
*A61P 27/02* (2006.01)

(52) U.S. Cl.
CPC ............ *A61K 31/47* (2013.01); *A61K 9/0048* (2013.01); *A61P 27/02* (2018.01)

(58) Field of Classification Search
CPC .. A61K 31/4709; A61K 31/47; C07D 215/48; C07D 215/52; C07D 405/04; C07D 413/12; A61P 27/02
See application file for complete search history.

(56) References Cited

U.S. PATENT DOCUMENTS

| 7,033,605 B2 * | 4/2006 | Wong ................... A61K 9/0051 424/427 |
| 2003/0212100 A1 | 11/2003 | Tsunoda et al. |
| 2006/0110428 A1 * | 5/2006 | deJuan ................ A61K 9/0051 424/427 |

FOREIGN PATENT DOCUMENTS

| CA | 2544404 A1 * | 6/2005 | ............. A61P 11/06 |
| WO | WO-2006094237 A2 * | 9/2006 | ............. A61P 27/02 |

OTHER PUBLICATIONS

Newman, Hereditary Optic Neuropathies: From the Mitochondria to the Optic Nerve, Sep. 2005, American Journal of Ophthalmology, 140, 517-523.*
Merck Manuals, Hereditary Optic Nerve Disorders, 2020, https://www.merckmanuals.com/home/eye-disorders/optic-nerve-disorders/hereditary-optic-nerve-disorders?query=leber%20hereditary%20optic%20neuropathy, printed Mar. 9, 2021, 2 pages.*
Altaweel, Best Disease: Treatments Medication, www.emedicine.com, Feb. 11, 2010, printed from http://emedicine.medscape.com/article/1227128-treatment, 2 pages.*
National Eye Institute, Facts About Retinopathy of Prematurity (ROP), Oct. 2009, printed from http://www.nei.nih.gov/health/rop/rop.asp#2, 6 pages.*
Www.WebMD.com, Retinal Detachment—Treatment Overview, Aug. 26, 2009, printed from http://www.webmd.com/eye-health/tc/retinal-detachment-treatment-overview, 2 pages.*
Danziger et al., Automated Site-directed Drug Design: A General Algorithm for Knowledge Acquisition about Hydrogen-Bonding Regions at Protein Surfaces, Mar. 22, 1989, The Royal Society, Proceedings of the Royal Society of London.Series B, Biological Sciences, vol. 236, No. 1283, p. 101-113.*
PUBCHEM CID-8593; "Cinchophen"; Mar. 26, 2005; 29 pages; U.S. National Library of Medicine.
Hu, Y., et al.; "Pathogenic role of diabetes-induces PPAR-a downregulation in microvascular dysfunction"; PNAS; Sep. 17, 2013; 110(38); 15401-15406.
PCT/US2017/030053; "International Search Report and Written Opinion"; Aug. 4, 2017; 12 pages.

* cited by examiner

*Primary Examiner* — Mark V Stevens
(74) *Attorney, Agent, or Firm* — Hall Estill Law Firm

(57) ABSTRACT

Compositions containing a phenylquinoline derivative compound having peroxisome proliferator-activated receptor a (PPARα) agonistic activity, and methods of their use in enhancing PPARα activity in retinal cells, and in treating ocular disorders or conditions, such as but not limited to retinal inflammation, retinal neovascularization, retinal vascular leakage, retinopathy of prematurity, diabetic retinopathy, age-related macular degeneration, and diabetic macular edema are disclosed.

5 Claims, 5 Drawing Sheets

PHENYLQUINOLINE COMPOSITIONS FOR TREATMENT OF OCULAR DISORDERS AND CONDITIONS

CROSS-REFERENCE TO RELATED APPLICATIONS

The present application is a national stage application of a PCT application having International Application No. PCT/US2017/030053, filed Apr. 28, 2017, which claims priority to U.S. Provisional Application having U.S. Serial No. 62/329,543, filed Apr. 29, 2016, which claims the benefit under 35 U.S.C. 119(e), the disclosure of which is hereby expressly incorporated herein by reference.

STATEMENT REGARDING FEDERALLY SPONSORED RESEARCH OR DEVELOPMENT

This invention was made with government support under Contract No. EY019309 awarded by the National Institutes of Health (NIH). The government has certain rights to the invention.

BACKGROUND

Retinal inflammation and resultant neovascularization (NV) are major causes of vision loss in a number of ocular disorders such as retinopathy of prematurity (ROP), diabetic retinopathy (DR) and age-related macular degeneration (AMD). Diabetic macular edema (DME) is caused by retinal vascular leakage and is the primary cause of vision loss in diabetic eye disease. Accumulating evidence suggests that DR is a chronic inflammatory disorder, as multiple inflammatory factors such as tumor necrosis factor-alpha (TNF-α), intercellular adhesion molecule-1 (ICAM-1), and vascular endothelial growth factor (VEGF) are over-expressed in the diabetic retina. Inflammation plays a causative role in impaired retinal vascular endothelial function, vascular leakage and later retinal NV.

The peroxisome proliferator-activated receptors (PPARs) are a family of nuclear hormone-activated receptors and transcription factors. The PPAR family includes three members, PPAR alpha (PPARα), PPAR beta (PPARβ), and PPAR gamma (PPARγ). Although these three PPAR members share significant sequence homology, they have different tissue distributions and diverse functions. While PPARγ is primarily expressed in adipose tissue, PPARα is expressed in cells with high mitochondrial activities including the liver, vascular endothelial cells (ECs), smooth muscle cells, kidney and heart. Preliminary studies have shown that PPARα is abundantly expressed in the retina. Upon activation by endogenous or exogenous synthetic agonists, PPARα forms a heterodimer with retinoid x receptor (RXR) and binds to the PPAR responsive element (PPRE) in the promoter of its target genes and, activating target gene transcription. In addition, PPARα indirectly regulates other genes by interfering with their transcriptional regulation. PPARα has been shown to regulate a large number of genes involved in lipid metabolism and vascular inflammation such as nuclear factor kappa-light-chain-enhancer of activated B cells (NF-κB), ICAM-1 and interleukin-6 (IL-6). Furthermore, PPARα has been shown to regulate oxidation and angiogenesis. However, the function of PPARα in the retina is poorly understood. The role of PPARα in DR was unrecognized until exciting findings from the FIELD and ACCORD clinical trials demonstrated that the PPARα agonist fenofibrate (a derivative of fenofibric acid) had a robust and unanticipated therapeutic effect on DR, reducing its by 32-40% in type 2 diabetic patients. Previous studies have demonstrated that PPARα levels are decreased in the retinae of both type 1 and type 2 diabetic animal models. Furthermore, activation of PPARα by fenofibrate effectively reduced retinal leukostasis and vascular leakage in diabetic models and ameliorates ischemia-induced retinal NV.

Fenofibrate was originally recognized for its ability to lower cholesterol and triglyceride levels and has thus been widely used clinically for the treatment of hyperlipidemia for more than 30 years. Fenofibrate is the first low-cost and safe oral drug for DR with clinically proven efficacy against NV and DME in DR patients and is thus of great interest to clinicians, basic scientists and pharmaceutical companies interested in the development of novel DR therapeutics. It has been reported that the protective effects of fenofibrate on retinal NV and DME are not correlated with its lipid-lowering activity, but the mechanism underlying its protective effects against DR is otherwise unknown. Fenofibrate thus has significant therapeutic potential in the treatment of DR and AMD, but has a relatively low binding affinity for PPARα, and has off-target nephrotoxic effects and other potential side effects. Development of higher affinity agonists of PPARα to further improve the treatment for DR and other inflammatory and angiogenic disorders of the eye is desirable and is the goal to which the present work is directed.

DETAILED DESCRIPTION

Figure 1:
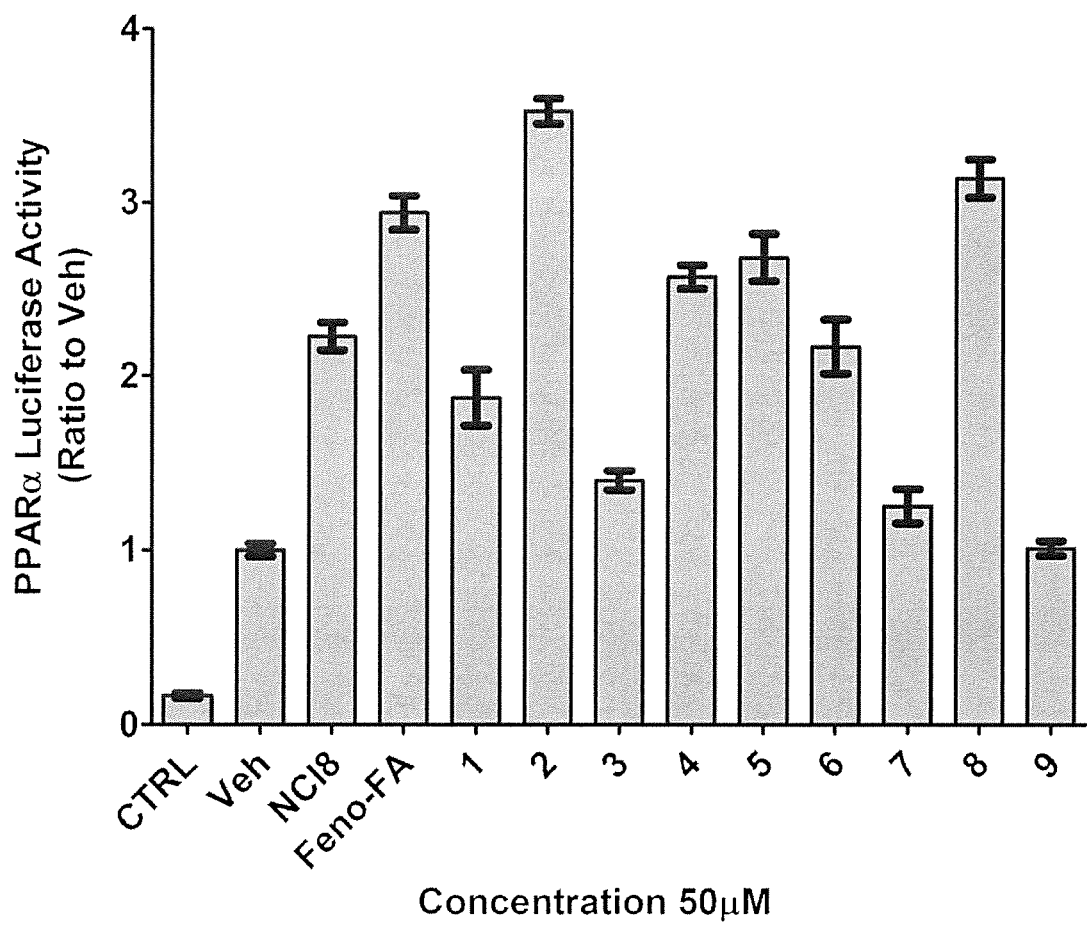
FIG. 1 shows the effect on PPARα transcriptional activity of Fenofibric acid (Feno-FA), NCI8 and compounds 1-9 of the present disclosure. The PPARα reporter Combo cells were treated with the indicated compounds at concentrations of 50 μM for 36 h, and then luciferase activities were measured.

As noted above, retinal inflammation and neovascularization are major causes of vision loss in a number of ocular disorders such as retinopathy of prematurity, diabetic retinopathy, and age-related macular degeneration. Two large, prospective clinical studies have reported fenofibrate, an agonist of PPARα, has robust therapeutic effects in DR. Disclosed herein is a new class of phenylquinolone derivatives, with a structure distinct from that of fenofibrate and Feno-FA, which due to PPARα agonistic activity, has an effect on retinal endothelial dysfunction, angiogenesis and inflammation, indicating a therapeutic effect in, for example, DR and AMD. The compositions of the present disclosure may be used in treatments for ocular disorder or conditions such as, but not limited to, retinal inflammation, retinal neovascularization (NV), retinal vascular leakage, retinopathy of prematurity (ROP), diabetic retinopathy (DR), age-related macular degeneration (AMD), and diabetic macular edema (DME).

Before further describing various embodiments of the compounds, compositions and methods of the present disclosure in more detail by way of exemplary description, examples, and results, it is to be understood that the compounds, compositions, and methods of present disclosure are not limited in application to the details of specific embodiments and examples as set forth in the following description. The description provided herein is intended for purposes of illustration only and is not intended to be construed in a limiting sense. As such, the language used herein is intended to be given the broadest possible scope and meaning; and the embodiments and examples are meant to be exemplary, not exhaustive. Also, it is to be understood that the phraseology and terminology employed herein is for the purpose of description and should not be regarded as limiting unless otherwise indicated as so. Moreover, in the following detailed description, numerous specific details are set forth in order to provide a more thorough understanding of the present disclosure. However, it will be apparent to a person having ordinary skill in the art that the present disclosure may be practiced without these specific details. In other instances, features which are well known to persons of ordinary skill in the art have not been described in detail to avoid unnecessary complication of the description. It is intended that all alternatives, substitutions, modifications and equivalents apparent to those having ordinary skill in the art are included within the scope of the present disclosure. All of the compounds, compositions, and methods of production and application and use thereof disclosed herein can be made and executed without undue experimentation in light of the present disclosure. Thus, while the compounds, compositions, and methods of the present disclosure have been described in terms of particular embodiments, it will be apparent to those of skill in the art that variations may be applied to the compounds, compositions and/or methods and in the steps or in the sequence of steps of the methods described herein without departing from the concept, spirit, and scope of the inventive concepts described herein.

All patents, published patent applications, and non-patent publications mentioned in the specification or referenced in any portion of this application are herein expressly incorporated by reference in their entirety to the same extent as if each individual patent or publication was specifically and individually indicated to be incorporated by reference.

Unless otherwise defined herein, scientific and technical terms used in connection with the present disclosure shall have the meanings that are commonly understood by those having ordinary skill in the art. Further, unless otherwise required by context, singular terms shall include pluralities and plural terms shall include the singular.

As utilized in accordance with the methods and compositions of the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or when the alternatives are mutually exclusive, although the disclosure supports a definition that refers to only alternatives and "and/or." The use of the term "at least one" will be understood to include one as well as any quantity more than one, including but not limited to, 2, 3, 4, 5, 6, 7, 8, 9, 10, 15, 20, 30, 40, 50, 100, or any integer inclusive therein. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z.

As used herein, all numerical values or ranges include fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth. Reference to a series of ranges includes ranges which combine the values of the boundaries of different ranges within the series. Thus, to illustrate reference to a series of ranges, for example, of 1-10, 10-20, 20-30, 30-40, 40-50, 50-60, 60-75, 75-100, 100-150, 150-200, 200-250, 250-300, 300-400, 400-500, 500-750, 750-1,000, includes ranges of 1-20, 10-50, 50-100, 100-500, and 500-1,000, for example.

As used in this specification and claims, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

Throughout this application, the term "about" is used to indicate that a value includes the inherent variation of error for the composition, the method used to administer the composition, or the variation that exists among the study subjects. As used herein the qualifiers "about" or "approximately" are intended to include not only the exact value, amount, degree, orientation, or other qualified characteristic or value, but are intended to include some slight variations due to measuring error, manufacturing tolerances, stress exerted on various parts or components, observer error, wear and tear, and combinations thereof, for example. The term "about" or "approximately", where used herein when referring to a measurable value such as an amount, a temporal duration, and the like, is meant to encompass, for example, variations of ±20%, or ±15%, or ±10%, or ±5%, or ±1%, or ±0.1% from the specified value, as such variations are appropriate to perform the disclosed methods and as understood by persons having ordinary skill in the art. As used herein, the term "substantially" means that the subsequently described event or circumstance completely occurs or that the subsequently described event or circumstance occurs to a great extent or degree. For example, the term "substantially" means that the subsequently described event or circumstance occurs at least 75% of the time, or at least 80% of the time, or at least 90% of the time, or at least 95% of the time, or at least 98% of the time.

As used herein any reference to "one embodiment" or "an embodiment" means that a particular element, feature, structure, or characteristic described in connection with the embodiment is included in at least one embodiment and may be included in other embodiments. The appearances of the phrase "in one embodiment" in various places in the specification are not necessarily all referring to the same embodiment and are not necessarily limited to a single or particular embodiment.

The term "pharmaceutically acceptable" refers to compounds and compositions which are suitable for administration to humans and/or animals without undue adverse side effects such as toxicity, irritation and/or allergic response commensurate with a reasonable benefit/risk ratio. The compounds of the present disclosure may be combined with one or more pharmaceutically-acceptable excipients, including carriers, vehicles, diluents, and adjuvents which may improve solubility, deliverability, dispersion, stability, and/or conformational integrity of the compounds or conjugates thereof.

As used herein, "pure," or "substantially pure" means an object species is the predominant species present (i.e., on a molar basis it is more abundant than any other object species in the composition thereof), and particularly a substantially purified fraction is a composition wherein the object species comprises at least about 50 percent (on a molar basis) of all macromolecular species present. Generally, a substantially pure composition will comprise more than about 80% of all macromolecular species present in the composition, more particularly more than about 85%, more than about 90%, more than about 95%, or more than about 99%. The term "pure" or "substantially pure" also refers to preparations where the object species is at least 60% (w/w) pure, or at least 70% (w/w) pure, or at least 75% (w/w) pure, or at least 80% (w/w) pure, or at least 85% (w/w) pure, or at least 90% (w/w) pure, or at least 92% (w/w) pure, or at least 95% (w/w) pure, or at least 96% (w/w) pure, or at least 97% (w/w) pure, or at least 98% (w/w) pure, or at least 99% (w/w) pure, or 100% (w/w) pure.

Non-limiting examples of animals within the scope and meaning of this term include dogs, cats, rats, mice, guinea pigs, chinchillas, horses, goats, cattle, sheep, zoo animals, Old and New World monkeys, non-human primates, and humans.

"Treatment" refers to therapeutic treatments. "Prevention" refers to prophylactic or preventative treatment measures or reducing the onset of a condition or disease. The term "treating" refers to administering the composition to a subject for therapeutic purposes and/or for prevention. Non-limiting examples of modes of administration include oral, topical, retrobulbar, subconjunctival, transdermal, parenteral, subcutaneous, intranasal, intramuscular, intraperitoneal, intravitreal, and intravenous routes, including both local and systemic applications. In addition, the compositions of the present disclosure may be designed to provide delayed, controlled, extended, and/or sustained release using formulation techniques which are well known in the art.

The term "topical" is used herein to define a mode of administration through an epithelial surface, such as but not limited to, a material that is administered by being applied externally to the eye. A non-limiting example of topical administration is through the use of eyedrops.

The terms "therapeutic composition" and "pharmaceutical composition" refer to a phenylquinoline derivative-containing composition that may be administered to a subject by any method known in the art or otherwise contemplated herein, wherein administration of the composition brings about a therapeutic effect as described elsewhere herein. In addition, the compositions of the present disclosure may be designed to provide delayed, controlled, extended, and/or sustained release using formulation techniques which are well known in the art.

The term "effective amount" refers to an amount of a phenylquinoline derivative which is sufficient to exhibit a detectable therapeutic or treatment effect in a subject without excessive adverse side effects (such as substantial toxicity, irritation and allergic response) commensurate with a reasonable benefit/risk ratio when used in the manner of the present disclosure. The effective amount for a subject will depend upon the subject's type, size and health, the nature and severity of the condition to be treated, the method of administration, the duration of treatment, the nature of concurrent therapy (if any), the specific formulations employed, and the like. Thus, it is not possible to specify an exact effective amount in advance. However, the effective amount for a given situation can be determined by one of ordinary skill in the art using routine experimentation based on the information provided herein. The term "activity-enhancing amount" refers to an amount of a phenylquinoline derivative which is sufficient to increase PPARα activity in a cell or subject.

The term "ameliorate" means a detectable or measurable improvement in a subject's condition or or symptom thereof. A detectable or measurable improvement includes a subjective or objective decrease, reduction, inhibition, suppression, limit or control in the occurrence, frequency, severity, progression, or duration of the condition, or an improvement in a symptom or an underlying cause or a consequence of the condition, or a reversal of the condition. A successful treatment outcome can lead to a "therapeutic effect," or "benefit" of ameliorating, decreasing, reducing, inhibiting, suppressing, limiting, controlling or preventing the occurrence, frequency, severity, progression, or duration of a condition, or consequences of the condition in a subject.

A decrease or reduction in worsening, such as stabilizing the condition, is also a successful treatment outcome. A therapeutic benefit therefore need not be complete ablation or reversal of the condition, or any one, most or all adverse symptoms, complications, consequences or underlying causes associated with the condition. Thus, a satisfactory endpoint may be achieved when there is an incremental improvement such as a partial decrease, reduction, inhibition, suppression, limit, control or prevention in the occurrence, frequency, severity, progression, or duration, or inhibition or reversal of the condition (e.g., stabilizing), over a short or long duration of time (e.g., seconds, minutes, hours).

Where used herein alkyls, alkoxyls, alkenyls, and alkynyls are generally intended to comprise 1, 2, 3, 4, 5, 6, 7, 8, 9, or 10 carbons, unless otherwise designated.

In at least certain embodiments, the present disclosure includes compositions and methods of treating ocular disorders and conditions, and particularly retinal conditions and disorders, which in certain non-limiting embodiments, include retinal inflammation, retinal neovascularization, retinal vascular leakage, retinopathy of prematurity (ROP), diabetic retinopathy (DR), age-related macular degeneration (AMD), and diabetic macular edema (DME) (or others disorders or conditions described elsewhere herein) using a phenylquinoline derivative compound having the chemical structure I:

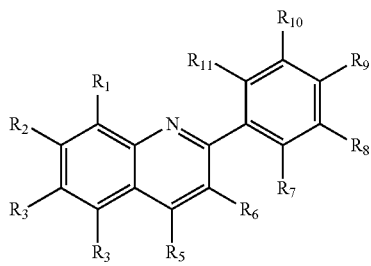

I

In at least certain embodiments, the $R_1$-$R_{11}$ substituents of chemical structure I are selected from, but not limited to, the group consisting of hydrogen (H), chlorine (Cl), fluorine (F), bromine (Br), iodine (I), cyano (CN), amino ($NH_2$), nitro ($NO_2$), alkoxy (e.g., $OCH_3$ or $OCH_2CH_3$), haloalkyl (e.g., $CF_3$), haloalkoxyl (e.g., $OCF_3$), substituted or unsubstituted alkyl, substituted or unsubstituted alkenyl, substituted or unsubstituted alkynyl, substituted or unsubstituted carbocycle, substituted or unsubstituted heterocycle, substituted or unsubstituted arene, substituted or unsubstituted heteroarene, $SO_3H$, an amide, thioamide, ester, thioester, a sulfonamide, a sulfinic acid, a sulfinamide, $SOR_a$, and $SO_2R_b$, wherein $R_a$ and $R_b$ are each selected from H, substituted or unsubstituted alkyl, substituted or unsubstituted arene, and substituted or unsubstituted heteroarene. Further, one of $R_7$-$R_8$, $R_8$-$R_9$, $R_9$-$R_{10}$, or $R_{10}$-$R_{11}$ may optionally comprise a dioxolane substituent in each compound. One of $R_4$ or $R_5$ comprises a carboxylic acid or carboxylic acid isostere as described in further detail below.

More particularly, examples substituents which can comprise the $R_1$-$R_{11}$ functional groups of chemical structure I include, but not limited to, the following:

(1)

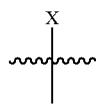

wherein X=H, F, Cl, Br, I, CN, $NH_2$, $NO_2$, $OCH_3$, $OCH_2CH_3$, $CF_3$, or $OCF_3$;

(2) a substituted or unsubstituted alkyl:

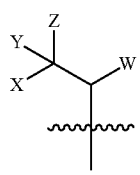

wherein W, X, Y, or Z=H, or X≠H;

(3) a haloalkyl:

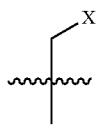

wherein X=F, Cl, Br, or I;

(4) a substituted or unsubstituted alkenyl:

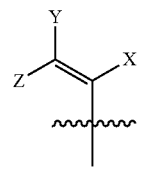

wherein X, Y, and Z=H, or X≠H;

(5) a substituted or unsubstituted alkynyl:

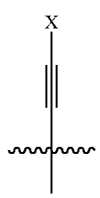

wherein X=H, or X≠H;

(6) a substituted or unsubstituted carbocycle or heterocycle:

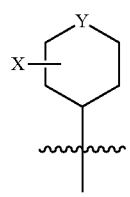

wherein Y=$CH_2$, O, NH, or S (at any position in the ring), and X=H or X≠H;

(7) a substituted or unsubstituted arene or heteroarene:

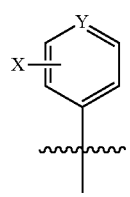

wherein Y=CH or N (at any position in the ring), and X=H or X≠H;

(8) an amide, ester, or thioester:

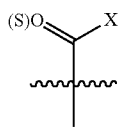

wherein X=OH, NH$_2$, OCH$_3$, NHalkyl, N-dialkyl, or SCH$_3$;

(9) a sulfonamide:

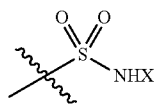

wherein X=H, or X≠H;

(10) a sulfinic acid or sulfinamide:

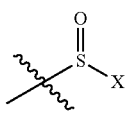

wherein X=OH, NH$_2$, NHalkyl, or N-dialkyl; and

(11) a thioamide:

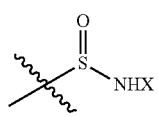

wherein X=NH$_2$, NHalkyl, or N-dialkyl.

As noted, in certain non-limiting embodiments, two consecutive substituents of R$_7$-R$_{11}$ (i.e., R$_7$-R$_8$, R$_8$-R$_9$, R$_9$-R$_{10}$, or R$_{10}$-R$_{11}$) may each comprise an oxygen (O), wherein the two O are linked by a carbon (C) forming a dioxolane substituent on the benzene ring such as indicated below:

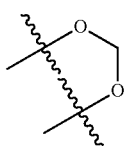

As noted above, in the presently disclosed compounds having chemical structure I, one of R$_4$ or R$_5$ (but not both of R$_4$ and R$_5$) comprises a substituent selected from the group consisting of carboxylic acid, and carboxylic acid isosteres including hydroxamic acid, hydroxamic ester, phosphonic acid, phosphinic acid, sulfonic acid, sulfinic acid, sulfonamide, acyl sulfonamide, sulfonylurea, acylurea, tetrazole, thiazolidine dione, oxazolidine dione, oxadiazol-5(4H)-one, thiadiazol-5(4H)-one, oxathiadiazole-2-oxide, oxadiazol-5(4H)-thione, isoxazole, tetramic acid, cyclopentane 1,3-diones, cyclopentane 1,2-diones, squaric acid derivatives, substituted phenols, heteroarene, amidine, hydroxyamide, alkyl hydroxyamidine, and salts of any of the above. Non-limiting examples of such substituents for R$_4$ and R$_5$ are further described below in Table 1.

TABLE 1

Examples of R$_4$ or R$_5$ substituents.

| R$_4$ or R$_5$ | Example Structure (n = 0-4) |
|---|---|
| Carboxylic acid | (structure) |
| Hydroxamic acid | (structure) |
| | (structure) |
| Hydroxamic ester | (structure) |
| | (structure) |
| Phosphonic acid | (structure) |
| Phosphinic acid | (structure) |
| Sulfonic acid | (structure) |
| Sulfinic acid | (structure) |
| Sulfonamide | (structure) |
| | (structure) |
| Acyl sulfonamide | (structure) |
| | (structure) |

TABLE 1-continued

Examples of $R_4$ or $R_5$ substituents.

| $R_4$ or $R_5$ | Example Structure (n = 0-4) |
|---|---|
| Sulfonylurea | 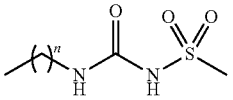 |
| Acylurea | 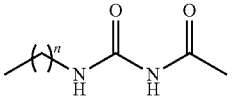 |
| Tetrazole | 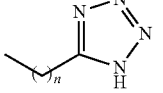 |
| Thiazolidine dione | 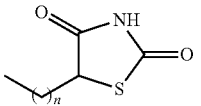 |
| Oxazolidine dione | 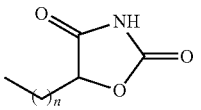 |
| Oxadiazol-5(4H)-one | 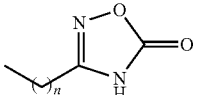 |
| Thiadiazol-5(4H)-one | 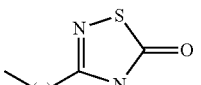 |
| Oxathiadiazole-2-oxide | 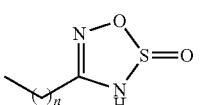 |
| Oxadiazole-5(4H)-thione | 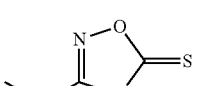 |
| Isoxazole | 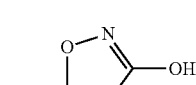 |
| Tetramic acid | 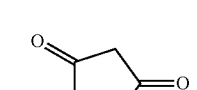 |
| Cyclopentane 1,3-dione | 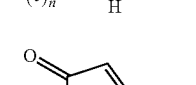 |

TABLE 1-continued

Examples of $R_4$ or $R_5$ substituents.

| $R_4$ or $R_5$ | Example Structure (n = 0-4) |
|---|---|
| | 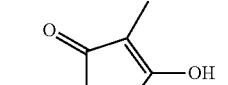 |
| | 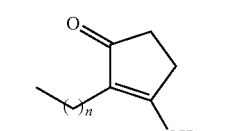 |
| Cyclopentane 1,2-dione | 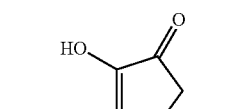 |
| |  |
| Squaric acid | 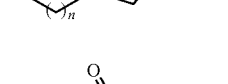 |
| | 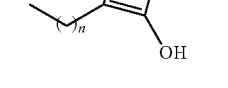 |
| Substituted phenol | 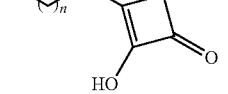 |
| | 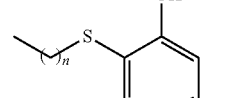 |
| | 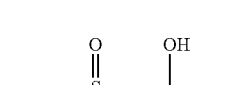 |

TABLE 1-continued

Examples of $R_4$ or $R_5$ substituents.

| $R_4$ or $R_5$ | Example Structure (n = 0-4) |
|---|---|
| | ![structure with F, OH, F on benzene ring] |
| | ![structure with F, OH, F on benzene ring] |
| heteroarene | ![5-membered ring with X] X = O, NH, S |
| | ![5-membered ring with X] X = O, NH, S |
| | ![5-membered ring with N and X] X = O, S |
| Amidine | ![amidine structure] |
| Hydroxyamide | ![hydroxyamide structure] |
| Alkyl hydroxyamidine | ![alkyl hydroxyamidine structure] |

In at least one embodiment, the phenylquinoline derivative compound used in the presently disclosed methods is NCI8, having chemical structure I wherein $R_1$ is a methyl group, $R_2$ is Cl, $R_5$ is a carboxylic acid (COOH), and $R_3$, $R_4$, $R_6$, $R_7$, $R_8$, $R_9$, $R_{10}$, and $R_{11}$ are H (chemical name: 7-chloro-8-methyl-2-phenylquinoline-4-carboxylic acid).

In at least embodiment the present disclosure includes and uses a composition that does not comprise NCI8 (7-chloro-8-methyl-2-phenylquinoline-4-carboxylic acid).

In certain non-limiting embodiments of the present disclosure, the compound has structure I, wherein $R_1$ is H or alkyl; $R_2$ and $R_3$ are independently selected from H, Cl, F, Br, and I; one of $R_4$ and $R_5$ is carboxylic acid and one of $R_4$ and $R_5$ is H; $R_6$ is selected from H, Cl, F, Br, and I; and $R_7$, $R_8$, $R_9$, $R_{10}$, and $R_{11}$ are independently selected from H, Cl, F, Br, OH, and alkoxy.

In certain non-limiting embodiments of the present disclosure, the compound has structure I, wherein $R_1$, $R_2$ and $R_3$ are independently selected from H, Cl, F, Br, I, and alkyl; $R_4$ is H; $R_5$ is carboxylic acid; $R_6$ is selected from H, Cl, F, Br, and I; and $R_7$, $R_8$, $R_9$, $R_{10}$, and $R_{11}$ are independently selected from H, Cl, F, Br, OH, and alkoxy.

In certain non-limiting embodiments of the present disclosure, the compound has structure I, wherein $R_1$, $R_2$ and $R_3$ are independently selected from H, Cl, F, Br, and I; $R_4$ is H; $R_5$ is carboxylic acid; $R_6$ is selected from H, Cl, F, Br, and I; and $R_7$, $R_8$, $R_9$, $R_{10}$, and $R_{11}$ are independently selected from H, OH, and methoxy.

In certain non-limiting embodiments of the present disclosure, the compound has structure I, wherein $R_1$, $R_2$, $R_3$ and $R_4$ are H; $R_5$ is carboxylic acid; $R_6$ is H; and $R_7$, $R_8$, $R_9$, $R_{10}$, and $R_{11}$ are selected from H, OH, and methoxy, wherein at least one of $R_7$, $R_8$, $R_9$, $R_{10}$, and $R_{11}$ is OH.

In certain non-limiting embodiments of the present disclosure, the compound has structure I, wherein $R_1$, $R_2$, $R_3$ and $R_4$ are H; $R_5$ is carboxylic acid; $R_6$ is H; and $R_7$, $R_8$, $R_9$, $R_{10}$, and $R_{11}$ are selected from H, OH, and methoxy, wherein at least one of $R_7$ and $R_{11}$ is OH.

In certain non-limiting embodiments of the present disclosure, the compound has structure I, wherein $R_1$, $R_2$, $R_3$ and $R_4$ are H; $R_5$ is carboxylic acid; $R_6$ is H; and $R_7$, $R_8$, $R_9$, $R_{10}$, and $R_{11}$ are selected from H and OH, wherein one of $R_7$ and $R_{11}$ is OH and one of $R_7$ and $R_{11}$ is H.

In certain non-limiting embodiments of the present disclosure, the compound has structure I, wherein $R_1$, $R_2$, $R_3$ and $R_4$ are H; $R_5$ is carboxylic acid; $R_6$ is H; and $R_7$, $R_8$, $R_9$, $R_{10}$, and $R_{11}$ are selected from H, OH, and methoxy, wherein at least one of $R_7$, $R_8$, $R_9$, $R_{10}$, and $R_{11}$ is methoxy.

In certain non-limiting embodiments of the present disclosure, the compound has structure I, wherein $R_1$, $R_2$, $R_3$ and $R_4$ are H; $R_5$ is carboxylic acid; $R_6$ is H; $R_7$ and $R_{11}$ are H; and $R_8$, $R_9$, and $R_{10}$ are selected from H and methoxy.

In certain non-limiting embodiments of the present disclosure, the compound has structure I, wherein $R_1$, $R_2$, $R_3$ and $R_4$ are H; $R_5$ is carboxylic acid; $R_6$ is H; $R_7$ and $R_{11}$ are H; and $R_8$, $R_9$, and $R_{10}$ are selected from H and methoxy, and $R_8$ and $R_9$ are methoxy and $R_{10}$ is H, or $R_8$ is H and $R_9$ and $R_{10}$ are methoxy.

More particularly, some non-limiting examples of compounds of the present disclosure (NCI8 and compounds 1-13) are shown below:

NCI8

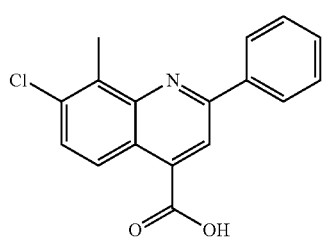

1

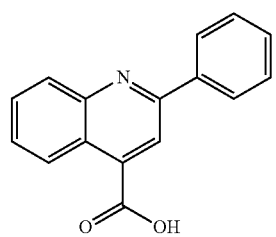

-continued
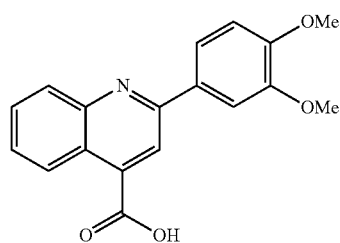
2
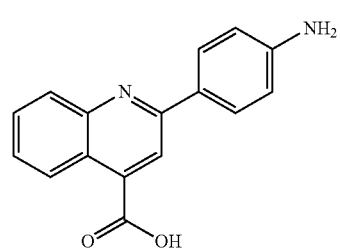
3
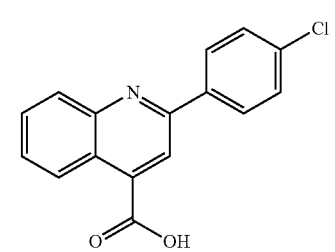
4
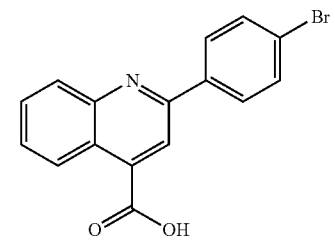
5
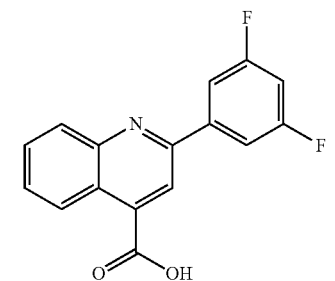
6
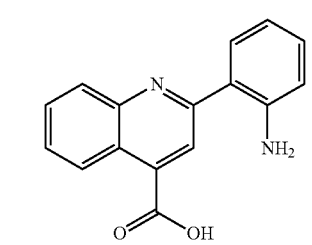
7
-continued
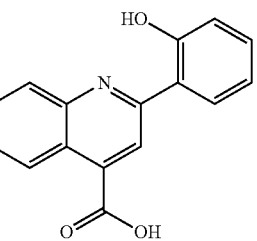
8
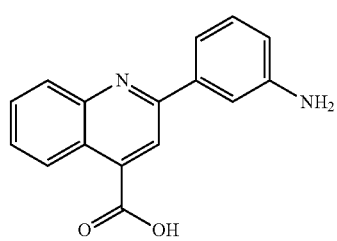
9
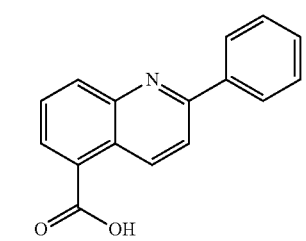
10
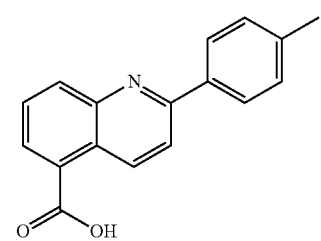
11
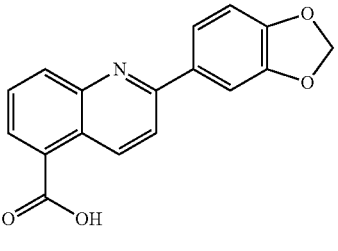
12
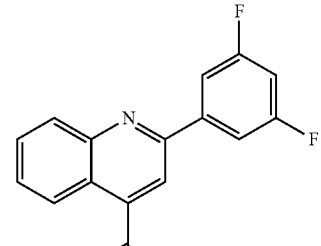
13
Other non-limiting examples of compounds in accordance with the present disclosure are shown below in Table 2.

TABLE 2

Examples of 2-Phenylquinoline Derivatives based on Chemical Structure I.

| No. | $R_1$ | $R_2$ | $R_3$ | $R_4$ | $R_5$ | $R_6$ | $R_7$ | $R_8$ | $R_9$ | $R_{10}$ | $R_{11}$ |
|---|---|---|---|---|---|---|---|---|---|---|---|
| NCI8 | $CH_3$ | Cl | H | H | COOH | H | H | H | H | H | H |
| 1 | H | H | H | H | COOH | H | H | H | H | H | H |
| 2 | H | H | H | H | COOH | H | H | $OCH_3$ | $OCH_3$ | H | H |
| 3 | H | H | H | H | COOH | H | H | H | $NH_2$ | H | H |
| 4 | H | H | H | H | COOH | H | H | H | Cl | H | H |
| 5 | H | H | H | H | COOH | H | H | H | Br | H | H |
| 6 | H | H | H | H | COOH | H | H | F | H | F | H |
| 7 | H | H | H | H | COOH | H | $NH_2$ | H | H | H | H |
| 8 | H | H | H | H | COOH | H | OH | H | H | H | H |
| 9 | H | H | H | H | COOH | H | H | $NH_2$ | H | H | H |
| 10 | H | H | H | COOH | H | H | H | H | H | H | H |
| 11 | H | H | H | COOH | H | H | H | $CH_3$ | H | H | H |
| 12 | H | H | H | COOH | H | H | Dioxolane[1] | | H | | |
| 13 | H | H | H | H | COOH | H | H | F | H | F | H |
| 14 | H | H | H | COOH | H | H | $OCH_3$ | H | $OCH_3$ | H | H |
| 15 | H | H | H | H | COOH | H | $OCH_3$ | H | $OCH_3$ | H | H |
| 16 | $CH_3$ | Cl | H | COOH | H | H | $OCH_3$ | H | $OCH_3$ | H | H |
| 17 | $CH_3$ | Cl | H | H | COOH | H | $OCH_3$ | H | $OCH_3$ | H | H |
| 18 | ![phenyl] | H | H | COOH | H | H | $OCH_3$ | H | $OCH_3$ | H | H |
| 19 | ![4-methylphenyl] | H | H | COOH | H | H | $OCH_3$ | H | $OCH_3$ | H | H |
| 20 | ![4-methoxyphenyl] | H | H | COOH | H | H | $OCH_3$ | H | $OCH_3$ | H | H |
| 21 | Cl | H | H | COOH | H | H | $OCH_3$ | H | $OCH_3$ | H | H |
| 22 | H | H | H | $CONH_2$ | H | H | | H | H | H | H |
| 23 | H | H | H | $CO_2Me$ | H | H | | H | H | H | H |
| 24 | H | H | H | $CONHNH_2$ | H | H | H | H | H | H | H |
| 25 | ![benzodioxole] | H | H | H | COOH | H | $OCH_3$ | H | H | $OCH_3$ | H |
| 26 | ![benzyl] | H | H | H | COOH | H | H | H | H | H | H |
| 27 | ![phenoxy] | H | H | H | COOH | H | H | H | H | H | H |
| 28 | ![phenylthio] | H | H | H | COOH | H | H | H | H | H | H |

TABLE 2-continued

Examples of 2-Phenylquinoline Derivatives based on Chemical Structure I.

| No. | $R_1$ | $R_2$ | $R_3$ | $R_4$ | $R_5$ | $R_6$ | $R_7$ | $R_8$ | $R_9$ | $R_{10}$ | $R_{11}$ |
|---|---|---|---|---|---|---|---|---|---|---|---|
| 29 | *N-phenyl (NH-C₆H₅)* | H | H | H | COOH | H | H | H | H | H | H |
| 30 | *4-hydroxyphenyl* | H | H | H | COOH | H | H | H | H | H | H |
| 31 | *4-propoxyphenyl* | H | H | H | COOH | H | H | H | H | H | H |
| 32 | *4-[2-(5-methyloxazol-4-yl)ethoxy]phenyl* | H | H | H | COOH | H | H | H | H | H | H |
| 33 | *4-[2-(5-methyl-2-phenyloxazol-4-yl)ethoxy]phenyl* | H | H | H | COOH | H | H | H | H | H | H |
| 34 | *4-[2-(5-methyl-2-phenyloxazol-4-yl)ethoxy]phenyl* | Cl | H | H | COOH | H | H | H | H | H | H |
| 35 | H | H | H | $CH_3$ | H | COOH | H | H | H | H | H | H |
| 36 | H | H | H | F | H | COOH | H | H | H | H | H | H |
| 37 | H | H | H | Br | H | COOH | H | H | H | H | H | H |
| 38 | H | H | H | H | H | COOH | $CH_3$ | H | H | H | H | H |
| 39 | H | H | H | H | H | COOH | F | H | H | H | H | H |
| 40 | H | H | H | H | H | COOH | Br | H | H | H | H | H |
| 41 | H | H | H | H | H | COOH | H | Dioxolane[2] | H | H | H |
| 42 | H | H | H | H | H | COOH | H | H | Dioxolane[3] | H |
| 43 | H | H | H | H | H | COOH | H | H | H | Dioxolane[4] |
| 44 | H | H | H | H | H | COOH | H | H | H | $SO_2NH_2$ | H | H |

[1]$R_8$ and $R_9$ together form a dioxolane structure;
[2]$R_7$ and $R_8$ together form a dioxolane;
[3]$R_9$ and $R_{10}$ together form a dioxolane;
[4]$R_{10}$ and $R_{11}$ together form a dioxolane.

Certain non-limiting embodiments of the present disclosure include pharmaceutical compositions that include at least one pharmaceutically acceptable carrier in combination with one or more phenylquinoline derivatives described herein (such as but are not limited to 7-chloro-8-methyl-2-phenylquinoline-4-carboxylic acid, compound 2: 2-(3,4-dimethoxyphenyl) quinoline-4-carboxylic acid, and compound 8: 2-(2-hydroxyphenyl) quinoline-4-carboxylic acid) that are agonists of PPARα and have anti-inflammatory and anti-angiogenic activities in the eye, particularly in the retina and macula. Particular non-limiting examples of pharmaceutical (therapeutic) compositions formulated in accordance with the present disclosure include: (a) a pharmaceutical composition comprising a phenylquinoline derivative PPARα agonist in combination with at least one pharmaceutically acceptable carrier; and (b) a phenylquinoline derivative PPARα agonist in combination with at least one other therapeutically active agent, and at least one pharmaceutically acceptable carrier.

The phenylquinoline derivatives of the present disclosure may be present in the pharmaceutical compositions at any concentration that allows the pharmaceutical composition to function in accordance with the present disclosure; for example, but not by way of limitation, the compound(s) may be present in a range having a lower level selected from 0.0001%, 0.005%, 0.001%, 0.005%, 0.01%, 0.05%, 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9% and 2.0%; and an upper level selected from 3%, 3.5%, 4%, 4.5%, 5%, 5.5%, 6%, 6.5%, 7%, 7.5%, 8%, 8.5%, 9%, 9.5%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, and 95%. Non-limiting examples of particular ranges include a range of from about 0.0001% to about 95%, a range of from about 0.001% to about 75%; a range of from about 0.005% to about 50%; a range of from about 0.01% to about 40%; a range of from about 0.05% to about 35%; a range of from about 0.1% to about 30%; a range of from about 0.1% to about 25%; a range of from about 0.1% to about 20%; a range of from about 1% to about 15%; a range of from about 2% to about 12%; a range of from about 5% to about 10%; and the like. Any other range that includes a lower level selected from the above-listed lower level concentrations and an upper level selected from the above-listed upper level concentrations also falls within the scope of the present disclosure.

Suitable carriers, vehicles, and other components that may be included in the formulation are described, for example, in *Remington: The Science and Practice of Pharmacy*, $21^{st}$ Ed. and $22^{nd}$ Ed. The term "pharmaceutically acceptable" means that the carrier is a non-toxic material that does not interfere with the effectiveness of the biological activity of the active agent. The characteristics of the carrier will depend on various factors, including but not limited to, the route of administration.

For example, but not by way of limitation, the phenylquinoline derivatives may be dissolved in a physiologically acceptable pharmaceutical carrier or diluent and administered as either a solution or a suspension. Non-limiting examples of suitable pharmaceutically acceptable carriers include water, saline, dextrose solutions, fructose solutions, ethanol, or oils of animal, vegetative, or synthetic origin, or any combination thereof. A sterile diluent, which may contain materials generally recognized for approximating physiological conditions and/or as required by governmental regulations, may be employed as the pharmaceutically acceptable carrier. In this respect, the sterile diluent may contain a buffering agent to obtain a physiologically acceptable pH, such as (but not limited to) sodium chloride, saline, phosphate-buffered saline, and/or other substances which are physiologically acceptable and/or safe for use.

The pharmaceutical compositions may also contain one or more additional components in addition to the phenylquinoline derivatives and pharmaceutically acceptable carrier(s) (and other additional therapeutically active agent(s), if present). Examples of additional components that may be present include, but are not limited to, diluents, fillers, salts, buffers, preservatives, stabilizers, solubilizers, and other materials well known in the art. Another particular non-limiting example of an additional component that may be present in the pharmaceutical composition is a delivery agent, as discussed in further detail herein below.

Other embodiments of the pharmaceutical compositions of the present disclosure may include the incorporation or entrapment of the therapeutic compound(s) in various types of drug delivery systems that function to provide targeted delivery, controlled release, and/or increased half-life to the therapeutic compound(s). For example, but not by way of limitation, it is possible to entrap the therapeutic compound(s) in microcapsules prepared by coacervation techniques or by interfacial polymerization (for example, hydroxymethylcellulose or gelatin-microcapsules and poly-(methylmethacylate) microcapsules, respectively). It is also possible to entrap the therapeutic compound(s) in macro-emulsions or colloidal drug delivery systems (such as but not limited to, liposomes, albumin microspheres, microemulsions, nanoparticles, nanocapsules, and the like). Such techniques are well known to persons having ordinary skill in the art, and thus no further description thereof is deemed necessary.

In one particular, non-limiting example, the pharmaceutical composition may include a liposome in which the phenylquinoline derivative PPARα agonist is disposed. In addition to other pharmaceutically acceptable carrier(s), the liposome may contain amphipathic agents such as lipids which exist in an aggregated form as micelles, insoluble monolayers, liquid crystals, or lamellar layers in aqueous solution. Suitable lipids for liposomal formulation include, but are not limited to, monoglycerides, diglycerides, sulfatides, lysolecithin, phospholipids, saponin, bile acids, combinations thereof, and the like. Preparation of such liposomal formulations is well within the level of ordinary skill in the art, as disclosed, for example, in U.S. Pat. Nos. 4,235,871; 4,501,728; 4,837,028; and 4,737,323; the entire contents of each of which are incorporated herein by reference.

In other non-limiting examples, the pharmaceutical compositions of the present disclosure may be incorporated into particles of one or more polymeric materials, as this type of incorporation can be useful in controlling the duration of action of the therapeutic compounds by allowing for controlled release from the preparations, thus increasing the half-life thereof. Non-limiting examples of polymeric materials that may be utilized in this manner include polyesters, polyamides, polyamino acids, hydrogels, poly(lactic acid), ethylene vinylacetate copolymers, copolymer micelles of, for example, PEG and poly(l-aspartamide), and combinations thereof.

In certain non-limiting embodiments, the pharmaceutical composition containing the phenylquinoline derivatives may be in the form of an ophthalmic composition for topical application to an eye of a subject. The term "ophthalmic composition" as used herein will be understood to refer to any composition specifically formulated for direct and local administration to an eye of a patient. Said composition may be formulated for topical administration to the eye or for injection into the eye (i.e., intravitreal or intraocular injection). The ophthalmic composition may be provided in any formulation that allows for local administration thereof to the eye and allows the therapeutic compounds to function in accordance with the present disclosure. For example, but not by way of limitation, the ophthalmic composition may be provided in the form of a solution, drops, a mist/spray, plasters and pressure sensitive adhesives, an ointment, a lotion, a cream, a gel, lyophilized/spray-dried forms, and the like. In one particular non-limiting embodiment, the ophthalmic composition is provided in a form for topical application, such as but not limited to, an eyedrop formulation. The ophthalmic compositions of the present disclosure may vary according to the particular active agent(s) used, the desired drug release profile, the condition being treated, and/or the medical history of the patient. In addition, the ophthalmic compositions of the present disclosure may be designed to provide delayed, controlled, extended, and/or sustained release using formulation techniques which are well known in the art, and as explained elsewhere herein.

The pharmaceutical compositions described or otherwise contemplated herein may further comprise at least one delivery agent that assists in delivery of the phenylquinoline derivative(s) to a desired site of delivery; for example but not by way of limitation, at least one delivery agent may be included in an ophthalmic composition to assist in the penetration of a surface of an eye; in certain embodiments, the delivery agent may assist in delivery to a retina of the eye. For example, in order for a topical application to be effective, the composition may need to be able to penetrate the surface of the eye so that it can travel to the desired tissue. This may include penetrating the conjunctiva and/or the cornea.

When the ophthalmic composition containing the phenylquinoline derivative(s) is formulated for administration by injection, the composition may be in the form of a pyrogen-free, aqueous solution or suspension. The preparation of such solutions, having due regard to pH, isotonicity, stability, and the like, is well within the skill of one of ordinary skill in the art. Suitable carriers include, but are not limited to, biocompatible and pharmaceutically acceptable phosphate buffered saline solutions, which are particularly isotonic. For example, but not by way of limitation, a particular ophthalmic composition may contain, in addition to the therapeutic compound(s), an isotonic vehicle such as Sodium Chloride Injection, Ringer's Injection, Dextrose Injection, Dextrose and Sodium Chloride Injection, Lactated Ringer's Injection, or other vehicles as known in the art. In general, the material for intravenous injection in humans should conform to regulations established by the US Food and Drug Administration, which are available to those in the field.

In addition to the ophthalmic administrations discussed in detail herein above, the therapeutic compositions of the present disclosure may be formulated for administration by any other method known or otherwise contemplated in the art, as long as the route of administration allows for delivery of the therapeutic compounds so that the compounds can function in accordance with the present disclosure, i.e., as a PPARα agonist. Examples of other routes of administration include, but are not limited to, oral, topical, retrobulbar, subconjunctival, transdermal, parenteral, subcutaneous, intranasal, intramuscular, intraperitoneal, intravitreal, and intravenous routes, including both local and systemic application routes.

Another non-limiting embodiment of the present disclosure is directed to a kit that contain one or more of any of the pharmaceutical compositions described or otherwise contemplated herein. The kit may further contain a second agent as described herein above for use concurrently with the pharmaceutical composition(s). If the composition present in the kit is not provided in the form in which it is to be delivered, the kit may further contain a pharmaceutically (e.g., ophthalmically) acceptable carrier, vehicle, diluent, or other agent for mixing with the therapeutic compound(s) for preparation of the pharmaceutical composition. The kit including the composition and/or other reagents may also be packaged with instructions packaged for administration and/or dosing of the compositions contained in the kit. The instructions may be fixed in any tangible medium, such as printed paper, or a computer-readable magnetic or optical medium, or instructions to reference a remote computer data source such as a worldwide web page accessible via the internet.

The kit may contain single or multiple doses of the pharmaceutical composition(s). When multiple doses are present, the doses may be disposed in bulk within a single container, or the multiple doses may be disposed individually within the kit; that is, the pharmaceutical compositions may be present in the kit in unit dosage forms to facilitate accurate dosing. The term "unit dosage forms" as used herein refers to physically discrete units suitable as unitary dosages for human subjects and other mammals; each unit contains a predetermined quantity of active material calculated to produce the desired therapeutic effect, in association with a suitable pharmaceutical excipient. Typical unit dosage forms of liquid compositions include prefilled, premeasured ampules or syringes; for solid compositions, typical unit dosage forms include pills, tablets, capsules, or the like. In such compositions, the therapeutic compound(s) may sometimes be a minor component (from about 0.1 to about 50% by weight, such as but not limited to, from about 1 to about 40% by weight) with the remainder being various vehicles or carriers and processing aids helpful for forming the desired dosing form.

As is evident from the above, the therapeutic phenylquinoline derivatives of the present disclosure function as PPARα agonists for the treatment, inhibition, mitigation, and/or prevention of degenerative retinal disorders. Thus, certain non-limiting embodiments of the present disclosure include methods of treating, inhibiting, and/or reducing the occurrence of retinal degeneration due to retinal inflammation and neovascularization. One particular but non-limiting embodiment includes a method of treating, inhibiting, and/or reducing the occurrence of one or more pathologic ocular conditions associated with reduced PPARα activity in a subject. In the method, one or more of any of the pharmaceutical compositions described or otherwise contemplated herein is administered to a subject (such as, but not limited to, a mammal) that is experiencing retinal or macular degeneration or that is predisposed to developing retinal or macular degeneration, or other ocular condition or disorder. The pharmaceutical composition(s) is administered to the subject in an amount effective to have PPARα agonistic activity in the retina of at least one eye of the subject.

The pathologic ocular condition may be any of the conditions described herein above, and the pathologic ocular condition may be characterized by retinal and/or macular degeneration. In one embodiment, the pharmaceutical composition may be administered topically to an eye of the subject (such as, but not limited to, as an eyedrop). In an alternative embodiment, the pharmaceutical composition may be administered by ocular injection, or systemically.

The amount of the therapeutic composition that is effective in the treatment described herein can be determined by the attending diagnostician, as one of ordinary skill in the art, by the use of conventional techniques and by observing results obtained under analogous circumstances. In determining the therapeutically effective dose, a number of factors may be considered by the attending diagnostician, including, but not limited to: the species of the subject; its size, age, and general health; the specific retinal and/or ocular disease or other condition involved; the degree, involvement, and/or severity of the retinal degeneration; the response of the individual subject; the particular therapeutic compound(s) administered; the mode of administration; the bioavailability characteristics of the preparation administered; the dose regimen selected; the use of concomitant medication; and other relevant circumstances. A therapeutically effective amount of a pharmaceutical composition of the present disclosure also refers to an amount of the therapeutic compound which is effective in controlling and/or reducing the retinal or macular degeneration.

For example, but not by way of limitation, the therapeutically effective amount of a phenylquinoline derivative used in the present disclosure will generally contain sufficient active ingredient to deliver in a range of from about 0.01 µg/kg to about 10 mg/kg (weight of active ingredient/body weight of patient). For example, but not by way of limitation, the composition will deliver about 0.1 µg/kg to about 5 mg/kg, and more particularly about 1 µg/kg to about 1 mg/kg.

Practice of the method of the present disclosure may include administering to a subject a therapeutically effective amount of the pharmaceutical composition (containing the phenylquinoline derivative(s)) in any suitable systemic and/or local formulation, in an amount effective to deliver the dosages listed above. The dosage can be administered, for example, but not by way of limitation, on a one-time basis, or administered at multiple times (for example, but not by way of limitation, from one to five times per day, or once or twice per week). The pharmaceutical composition may be administered either alone or in combination with other therapies, in accordance with the inventive concepts disclosed herein.

Certain novel embodiments of the present disclosure, having now been generally described, will be more readily understood by reference to the following examples, which are included merely for purposes of illustration of certain aspects and embodiments of the present disclosure, and are not intended to be limiting. The following detailed examples are to be construed, as noted above, only as illustrative, and not as limiting of the present disclosure in any way whatsoever. Those skilled in the art will promptly recognize appropriate variations from the various compositions, structures, components, procedures and methods.

EXAMPLES

The anti-inflammatory and anti-angiogenic activities of the phenylquinoline derivative 7-chloro-8-methyl-2-phenylquinoline-4-carboxylic acid (also referred to herein also as NCI8) and others disclosed herein were investigated in vitro and in animal models. Prior to the present work NCI8, which is distinct in structure from the known PPARα agonist fenofibrate, had not been reported to have PPARα agonist activity.

Example 1

Methods

The activation of PPARα by NCI8 was measured by luciferase-based promoter assay. The effect of NCI8 on endothelial cell migration and tube formation was evaluated using human retinal capillary endothelial cells (HRCEC). TUNEL was used to evaluate the effect on apoptosis in human retinal Müller cells (MIO-M1) and retinal precursor cells (R28) exposed to palmitate. C57BL/6 mice were exposed to 75% oxygen from postnatal day 7 (P7) to P12, followed by exposure to room air from P12 to P17 to generate oxygen-induced retinopathy (OIR). NCI8 (10 mg/kg/day) and the same volume of vehicle were intraperitoneally injected daily from P12 to P16. At P17, retinal inflammation was examined using leukostasis assay, and retinal levels of inflammatory factors were measured by Western blotting. Student's T-test was used for statistical analysis.

Results

NCI8 activated PPARα transcriptional activity in a concentration-dependent manner (with EC50 of 49.89 µM compared to 53.01 µM of fenofibrate). HRCEC migration and tube formation were significantly inhibited. The compound also showed a protective effect against palmitate-induced apoptosis of human retinal Müller cells and retinal precursor cells. In the OIR model, the number of adherent leukocytes was decreased in the retinal vasculature of the mice treated with the compound compared to vehicle group (n=5, P<0.05). In addition, retinal levels of ICAM-1, monocyte chemoattractant protein-1 (MCP-1) and TNF-α were downregulated by this compound. NCI8 inhibited expression of VEGF, endothelial cell migration and tube formation with potencies similar to or higher than fenofibrate. Injection of NCI8 also ameliorated retinal capillary degeneration and pericyte loss in a diabetic model. Taken together, these in vivo results indicate that NCI8 has a robust anti-inflammatory and therapeutic effects in both OIR and diabetic models.

Particularly, NCI8 displayed the following effects to support its use as a therapeutic treatment for DR and AMD:
1. Potent effects in enhancing transcriptional activities of PPARα.
2. In human retinal capillary endothelial cells (HRCEC), inhibition of endothelial cell migration in a concentration-dependent manner in the range of 50-200 µM.
3. In HRCEC, inhibition of tube formation with a higher potency than fenofibric acid.
4. In ARPE19 cells, protection of RPE cells from cell death induced by palmitate, a commonly used diabetic stressor.
5. In the OIR model, daily intraperitoneal 10 mg/kg/day injections from postnatal day 12 (P12) to P16 significantly reduced retinal leukostasis.
6. Injection into mice with OIR significantly down-regulated MCP-1, ICAM-1 and TNF-α expression in the retina.
7. Treatment of streptozotocin-induced diabetic rats (i.p., 10 mg/kg/day, 3 weeks) decreased numbers of acellular capillaries in the retina, indicating a protective effect against diabetes-induced capillary degeneration.
8. Treatment of diabetic rats (i.p., 10 mg/kg/day, 3 weeks) significantly increased pericyte numbers, indicating a pericyte protective effect.

In summary, the in vitro and in vivo data of this example demonstrate that NCI8 has potent effects on activation of PPARα and robust anti-inflammatory and anti-angiogenic activities.

Example 2

Various phenylquinoline derivatives of the present disclosure were tested for their effects on PPARα transcriptional activity in PPARα reporter Combo cells, including NCI8 and compounds 1-13 as disclosed herein, as measured against the effect of Feno-FA.

Figure 2:
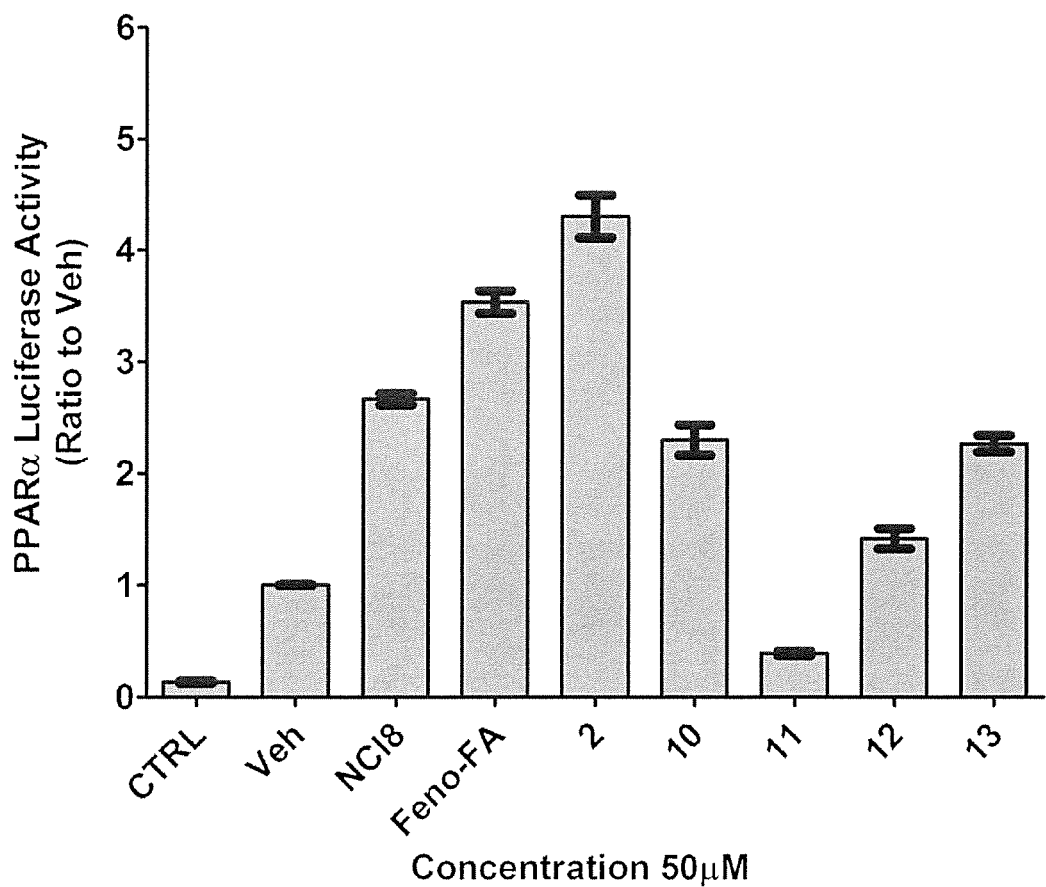
FIG. 2 shows the effect on PPARα transcriptional activity of Feno-FA, NCI8 and compounds 2 and 10-13 of the present disclosure. The PPARα reporter Combo cells were treated with indicated compounds at concentrations of 50 μM for 36 h, and then luciferase activities were measured.
Figure 3:
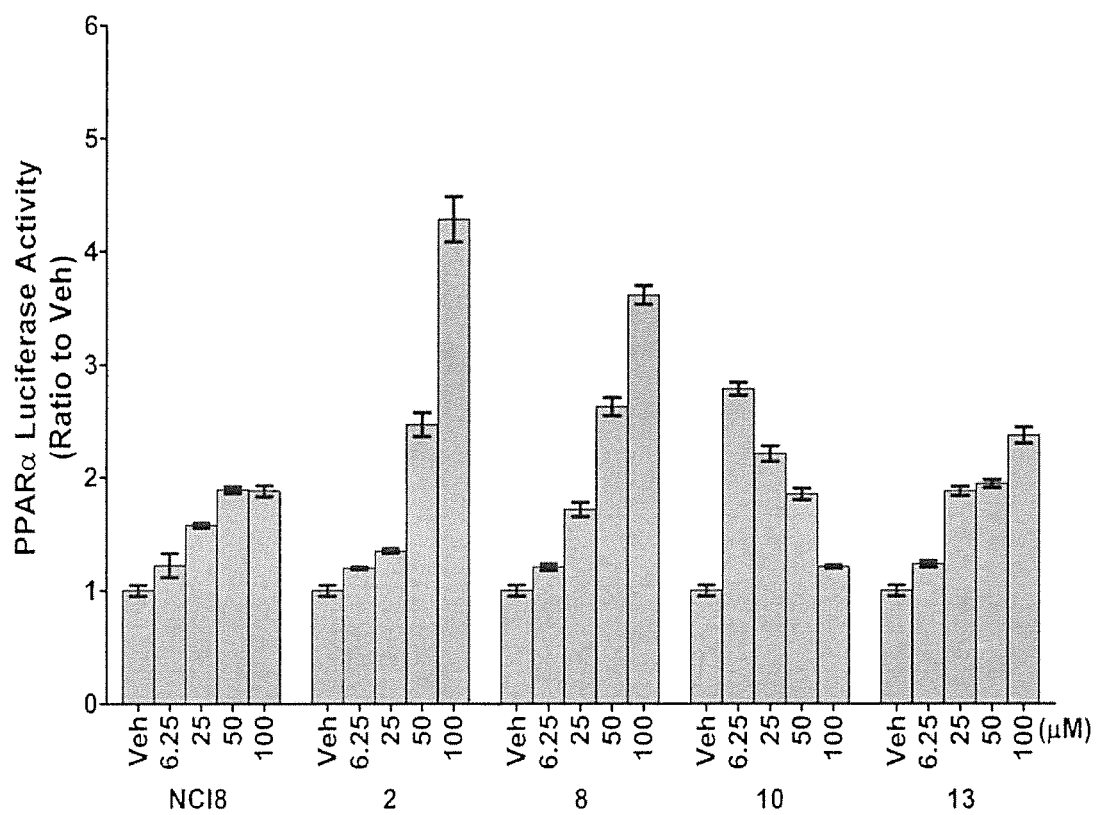
FIG. 3 shows the dose dependent effect on PPARα transcriptional activity PPARα reporter Combo cells after treatment by various concentrations of NCI8 and compounds 2, 8, 10, and 13 up to 100 μM for 36 h, after which luciferase activities were measured.
Figure 4:
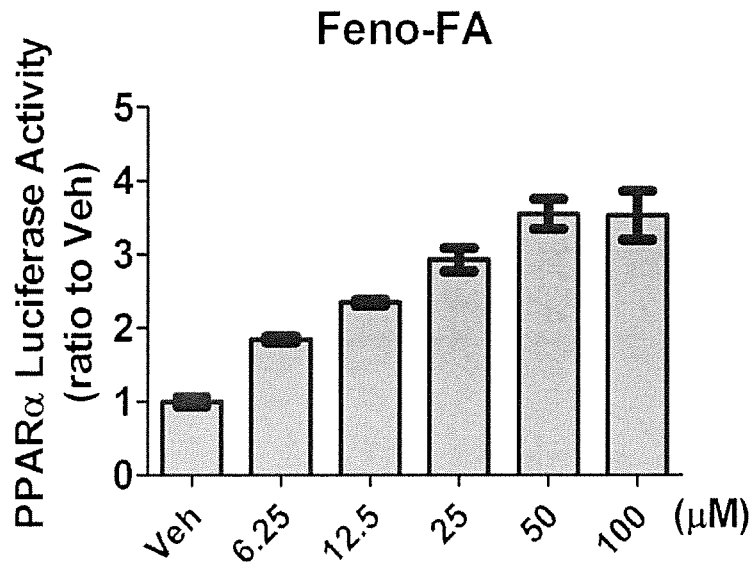
FIG. 4 shows the effect on PPARα transcriptional activity of Feno-FA in PPARα reporter Combo cells.
Figure 5:
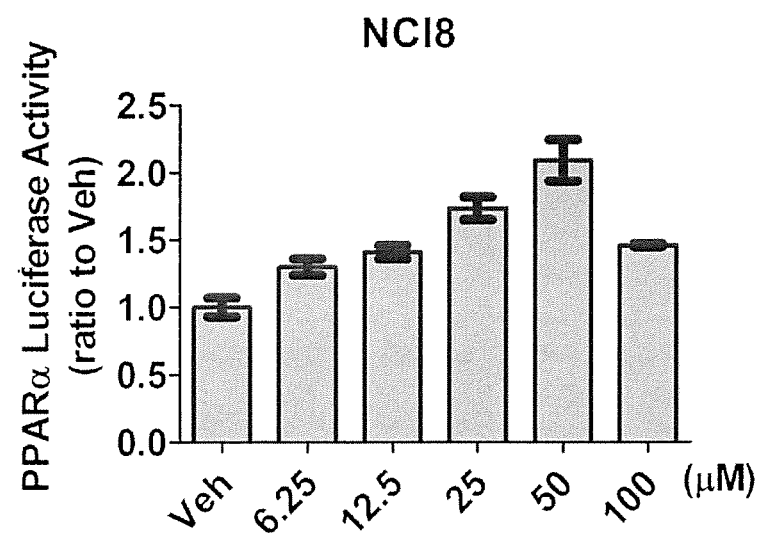
FIG. 5 shows the effect on PPARα transcriptional activity of NCI8 in PPARα reporter Combo cells.
Figure 6:
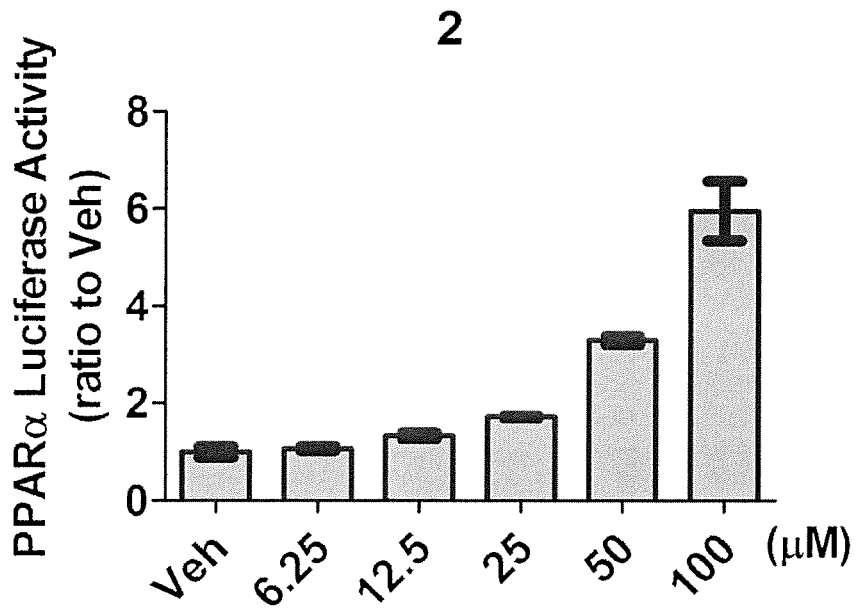
FIG. 6 shows the effect on PPARα transcriptional activity of compound 2 in PPARα reporter Combo cells.
Figure 7:
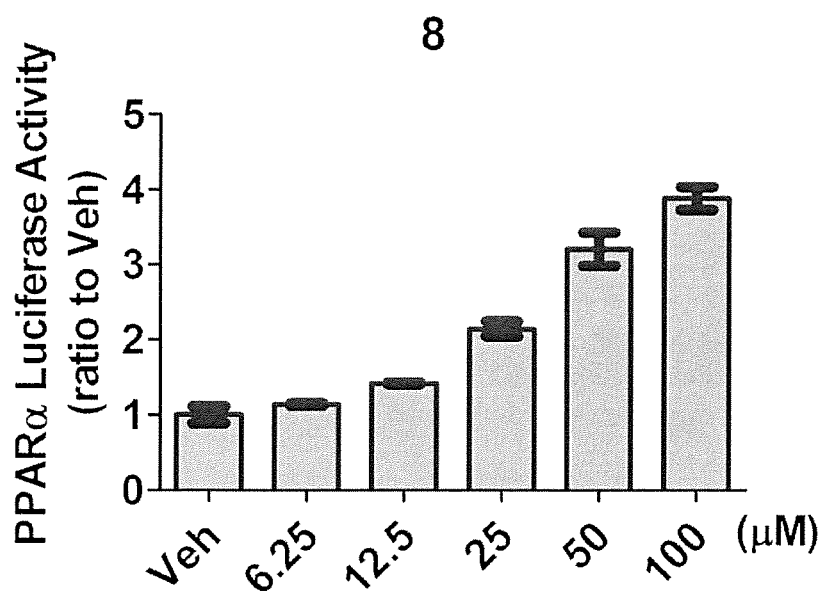
FIG. 7 shows the effect on PPARα transcriptional activity of compound 8 in PPARα reporter Combo cells.

FIG. 1 shows the effect on PPARα transcriptional activity of NCI8 and compounds 1-9. Cells were treated with various compounds at concentrations of 50 µM for 36 h, after which luciferase activities were measured. FIG. 2 shows the effect on PPARα transcriptional activity of NCI8 and compounds 2 and 10-13. Cells were treated with various compounds at concentrations of 50 µM for 36 h, after which luciferase activities were measured. Compounds 2 and 8 had the highest agonistic activity. FIG. 3 shows the dose dependent effect on PPARα transcriptional activity of various concentrations of NCI8 and compounds 2, 8, 10, and 13 up to 100 µM for 36 h, after which luciferase activities were measured. Compounds 2 and 8 had then greatest activity, replicating the results of FIG. 1. The experiments were repeated as various increasing concentrations comparing the effects of Feno-FA (FIG. 4), NCI8 (FIG. 5), compound 2 (FIG. 6), and compound 8 (FIG. 7). The results of FIG. 1 were substantially replicated, with compound 2 showing the greatest agonistic activity on PPARα transcription.

These studies demonstrate therapeutic use of ophthalmic compositions comprising this new class of phenylquinoline compounds for the treatment of ocular disorders and conditions such as but not limited to retinal inflammation, retinal neovascularization, retinal vascular leakage, retinopathy of prematurity, diabetic retinopathy, age-related macular degeneration, and diabetic macular edema.

In accordance with the foregoing, the present disclosure is directed, in at least some embodiments, to the following:

Clause 1. A method of increasing peroxisome proliferator-activated receptor α (PPARα) activity in a retinal cell, comprising:
administering to the retinal cell an activity-enhancing amount of a phenylquinoline derivative compound having peroxisome proliferator-activated receptor α (PPARα) agonistic activity, the compound having the chemical structure I:

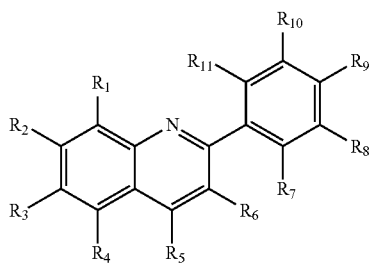

wherein:
(1) $R_1$, $R_2$, $R_3$, and $R_6$, are independently selected from the group consisting of
 (i) hydrogen (H), chlorine (Cl), fluorine (F), bromine (Br), iodine (I), cyano (CN), amino ($NH_2$), nitro ($NO_2$), alkoxy, haloalkyl, haloalkoxyl, substituted or unsubstituted alkyl, substituted or unsubstituted alkenyl, substituted or unsubstituted alkynyl, substituted or unsubstituted carbocycle, substituted or unsubstituted heterocycle, substituted or unsubstituted arene, substituted or unsubstituted heteroarene, $SO_3H$, an amide, thioamide, ester, thioester, a sulfonamide, a sulfinic acid, a sulfinamide, and
 (ii) $SOR_a$, and $SO_2R_b$, wherein $R_a$ and $R_b$ are each selected from H, substituted or unsubstituted alkyl, substituted or unsubstituted arene, and substituted or unsubstituted heteroarene;
(2) $R_7$, $R_8$, $R_9$, $R_{10}$, and $R_{11}$ are independently selected from the group consisting of (i), (ii), and (iii), wherein (iii) is a dioxolane formed from only one of the pairs $R_7$-$R_8$, $R_8$-$R_9$, $R_9$-$R_{10}$, and $R_{10}$-$R_{11}$; and
(3) $R_4$ and $R_5$ are selected from the group consisting of (i), (ii), and (iv), wherein (iv) consists of carboxylic acid, hydroxamic acid, hydroxamic ester, phosphonic acid, phosphinic acid, sulfonic acid, sulfonamide, a sulfinic acid, acyl sulfonamide, sulfonylurea, acylurea, tetrazole, thiazolidine dione, oxazolidine dione, oxadiazol-5(4H)-one, thiadiazol-5(4H)-one, oxathiadiazole-2-oxide, oxadiazol-5(4H)-thione, isoxazole, tetramic acid, cyclopentane 1,3-diones, cyclopentane 1,2-diones, a squaric acid, a substituted phenol, heteroarene, amidine, hydroxyamide, alkyl hydroxyamidine, and salts of the above; and with the proviso that one of $R_4$ and $R_5$ is selected from (i) and (ii), and one of $R_4$ and $R_5$ is selected from (iv).

Clause 2. The method of clause 1, wherein in the compound: $R_1$, $R_2$, $R_3$ and $R_4$ are H; $R_5$ is a carboxylic acid; $R_6$, $R_7$ and $R_{11}$ are H; and $R_8$ and $R_9$ are methoxy and $R_{10}$ is H, or $R_8$ is H and $R_9$ and $R_{10}$ are methoxy.

Clause 3. The method of clause 1, wherein in the compound: $R_1$, $R_2$, $R_3$, $R_4$ $R_6$, $R_8$, $R_9$, and $R_{10}$ are are H; $R_5$ is a carboxylic acid; and $R_7$ and $R_{11}$ are selected from H and OH with the provisio that at least one of $R_7$ and $R_{11}$ is OH.

Clause 4. The method of clause 1, wherein in the compound: $R_1$ is $CH_3$, $R_2$ is Cl, $R_5$ is a carboxylic acid group, and $R_3$, $R_4$, $R_6$, $R_7$, $R_8$, $R_9$, $R_{10}$, and $R_{11}$ are H.

Clause 5. The method of clause 1, wherein in the compound: $R_1$ is H or alkyl; $R_2$ and $R_3$ are independently selected from H, Cl, F, Br, and I; one of $R_4$ and $R_5$ is carboxylic acid and one of $R_4$ and $R_5$ is H; $R_6$ is selected from H, Cl, F, Br, and I; and $R_7$, $R_8$, $R_9$, $R_{10}$, and $R_{11}$ are independently selected from H, Cl, F, Br, OH, and alkoxy.

Clause 6. The method of clause 1, wherein in the compound: $R_1$, $R_2$ and $R_3$ are independently selected from H, Cl, F, Br, I, and alkyl; $R_4$ is H; $R_5$ is carboxylic acid; $R_6$ is selected from H, Cl, F, Br, and I; and $R_7$, $R_8$, $R_9$, $R_{10}$, and $R_{11}$ are independently selected from H, Cl, F, Br, OH, and alkoxy.

Clause 7. The method of clause 1, wherein in the compound: $R_1$, $R_2$ and $R_3$ are independently selected from H, Cl, F, Br, and I; $R_4$ is H; $R_5$ is carboxylic acid; $R_6$ is selected from H, Cl, F, Br, and I; and $R_7$, $R_8$, $R_9$, $R_{10}$, and $R_{11}$ are independently selected from H, OH, and methoxy.

Clause 8. The method of clause 1, wherein in the compound: $R_1$, $R_2$, $R_3$ and $R_4$ are H; $R_5$ is carboxylic acid; $R_6$ is H; and $R_7$, $R_8$, $R_9$, $R_{10}$, and $R_{11}$ are selected from H, OH, and methoxy, wherein at least one of $R_7$, $R_8$, $R_9$, $R_{10}$, and $R_{11}$ is OH.

Clause 9. The method of clause 1, wherein in the compound: $R_1$, $R_2$, $R_3$ and $R_4$ are H; $R_5$ is carboxylic acid; $R_6$ is H; and $R_7$, $R_8$, $R_9$, $R_{10}$, and $R_{11}$ are selected from H and OH, wherein one of $R_7$ and $R_{11}$ is OH and one of $R_7$ and $R_{11}$ is H.

Clause 10. The method of clause 1, wherein in the compound: $R_1$, $R_2$, $R_3$ and $R_4$ are H; $R_5$ is carboxylic acid; $R_6$ is H; and $R_7$, $R_8$, $R_9$, $R_{10}$, and $R_{11}$ are selected from H, OH, and methoxy, wherein at least one of $R_7$, $R_8$, $R_9$, $R_{10}$, and $R_{11}$ is methoxy.

Clause 11. The method of clause 1, wherein in the compound: $R_1$, $R_2$, $R_3$ and $R_4$ are H; $R_5$ is carboxylic acid; $R_6$ is H; $R_7$ and $R_{11}$ are H; and $R_8$, $R_9$, and $R_{10}$ are selected from H and alkoxy, wherein at least one of $R_8$, $R_9$, and $R_{10}$ is an alkoxy.

Clause 12. A method of treating an ocular disorder or condition in a subject in need of such therapy, comprising:
administering to the subject an effective amount of a composition comprising a phenylquinoline derivative compound having peroxisome proliferator-activated receptor α (PPARα) agonistic activity, the compound having the chemical structure I:

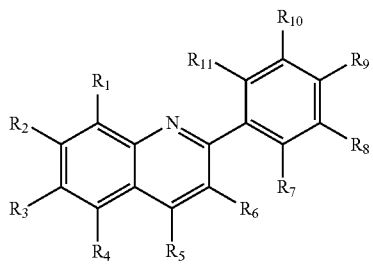

wherein:
(1) $R_1$, $R_2$, $R_3$, and $R_6$, are independently selected from the group consisting of
   (i) hydrogen (H), chlorine (Cl), fluorine (F), bromine (Br), iodine (I), cyano (CN), amino ($NH_2$), nitro ($NO_2$), alkoxy, haloalkyl, haloalkoxyl, substituted or unsubstituted alkyl, substituted or unsubstituted alkenyl, substituted or unsubstituted alkynyl, substituted or unsubstituted carbocycle, substituted or unsubstituted heterocycle, substituted or unsubstituted arene, substituted or unsubstituted heteroarene, SO3H, an amide, thioamide, ester, thioester, a sulfonamide, a sulfinic acid, a sulfinamide, and
   (ii) $SOR_a$, and $SO_2R_b$, wherein $R_a$ and $R_b$ are each selected from H, substituted or unsubstituted alkyl, substituted or unsubstituted arene, and substituted or unsubstituted heteroarene;
(2) $R_7$, $R_8$, $R_9$, $R_{10}$, and $R_{11}$ are independently selected from the group consisting of (i), (ii), and (iii), wherein
   (iii) is a dioxolane formed from only one of the group of pairs consisting of $R_7$-$R_8$, $R_8$-$R_9$, $R_9$—$R_{10}$, and $R_{10}$-$R_{11}$; and
(3) $R_4$ and $R_5$ are selected from the group consisting of (i), (ii), and (iv), wherein
   (iv) consists of carboxylic acid, hydroxamic acid, hydroxamic ester, phosphonic acid, phosphinic acid, sulfonic acid, sulfonamide, a sulfinic acid, acyl sulfonamide, sulfonylurea, acylurea, tetrazole, thiazolidine dione, oxazolidine dione, oxadiazol-5(4H)-one, thiadiazol-5(4H)-one, oxathiadiazole-2-oxide, oxadiazol-5(4H)-thione, isoxazole, tetramic acid, cyclopentane 1,3-diones, cyclopentane 1,2-diones, a squaric acid, a substituted phenol, heteroarene, amidine, hydroxyamide, alkyl hydroxyamidine, and salts of the above; and with the proviso that one of $R_4$ and $R_5$ is selected from (i) and (ii), and one of $R_4$ and $R_5$ is selected from (iv).

Clause 13. The method of clause 12, wherein in the compound: $R_1$, $R_2$, $R_3$ and $R_4$ are H; $R_5$ is a carboxylic acid; $R_6$, $R_7$ and $R_{11}$ are H; and $R_8$ and $R_9$ are methoxy and $R_{10}$ is H, or $R_8$ is H and $R_9$ and $R_{10}$ are methoxy.

Clause 14. The method of clause 12, wherein in the compound: $R_1$, $R_2$, $R_3$, $R_4$ $R_6$, $R_8$, $R_9$, and $R_{10}$ are are H; $R_5$ is a carboxylic acid; and $R_7$ and $R_{11}$ are selected from H and OH with the provisio that at least one of $R_7$ and $R_{11}$ is OH.

Clause 15. The method of clause 12, wherein in the compound: $R_1$ is $CH_3$, $R_2$ is Cl, $R_5$ is a carboxylic acid group, and $R_3$, $R_4$, $R_6$, $R_7$, $R_8$, $R_9$, $R_{10}$, and $R_{11}$ are H.

Clause 16. The method of clause 12, wherein in the compound: $R_1$ is H or alkyl; $R_2$ and $R_3$ are independently selected from H, Cl, F, Br, and I; one of $R_4$ and $R_5$ is carboxylic acid and one of $R_4$ and $R_5$ is H; $R_6$ is selected from H, Cl, F, Br, and I; and $R_7$, $R_8$, $R_9$, $R_{10}$, and $R_{11}$ are independently selected from H, Cl, F, Br, OH, and alkoxy.

Clause 17. The method of clause 12, wherein in the compound: $R_1$, $R_2$ and $R_3$ are independently selected from H, Cl, F, Br, I, and alkyl; $R_4$ is H; $R_5$ is carboxylic acid; $R_6$ is selected from H, Cl, F, Br, and I; and $R_7$, $R_8$, $R_9$, $R_{10}$, and $R_{11}$ are independently selected from H, Cl, F, Br, OH, and alkoxy.

Clause 18. The method of clause 12, wherein in the compound: $R_1$, $R_2$ and $R_3$ are independently selected from H, Cl, F, Br, and I; $R_4$ is H; $R_5$ is carboxylic acid; $R_6$ is selected from H, Cl, F, Br, and I; and $R_7$, $R_8$, $R_9$, $R_{10}$, and $R_{11}$ are independently selected from H, OH, and methoxy.

Clause 19. The method of clause 12, wherein in the compound: $R_1$, $R_2$, $R_3$ and $R_4$ are H; $R_5$ is carboxylic acid; $R_6$ is H; and $R_7$, $R_8$, $R_9$, $R_{10}$, and $R_{11}$ are selected from H, OH, and methoxy, wherein at least one of $R_7$, $R_8$, $R_9$, $R_{10}$, and $R_{11}$ is OH.

Clause 20. The method of clause 12, wherein in the compound: $R_1$, $R_2$, $R_3$ and $R_4$ are H; $R_5$ is carboxylic acid; $R_6$ is H; and $R_7$, $R_8$, $R_9$, $R_{10}$, and $R_{11}$ are selected from H and OH, wherein one of $R_7$ and $R_{11}$ is OH and one of $R_7$ and $R_{11}$ is H.

Clause 21. The method of clause 12, wherein in the compound: $R_1$, $R_2$, $R_3$ and $R_4$ are H; $R_5$ is carboxylic acid; $R_6$ is H; and $R_7$, $R_8$, $R_9$, $R_{10}$, and $R_{11}$ are selected from H, OH, and methoxy, wherein at least one of $R_7$, $R_8$, $R_9$, $R_{10}$, and $R_{11}$ is methoxy.

Clause 22. The method of clause 12, wherein in the compound: $R_1$, $R_2$, $R_3$ and $R_4$ are H; $R_5$ is carboxylic acid; $R_6$ is H; $R_7$ and $R_{11}$ are H; and $R_8$, $R_9$, and $R_{10}$ are selected from H and alkoxy, wherein at least one of $R_8$, $R_9$, and $R_{10}$ is an alkoxy.

Clause 23. The method of any one of clauses 12-22, wherein the ocular disorder or condition is selected from the group consisting of retinal inflammation, retinal neovascularization, retinal vascular leakage, retinopathy of prematurity (ROP), diabetic retinopathy (DR), age-related macular degeneration (AMD), and diabetic macular edema (DME).

Clause 24. An ophthalmic composition, comprising a pharmaceutically-acceptable carrier, vehicle, or diluent; and a phenylquinoline derivative compound having peroxisome proliferator-activated receptor α (PPARα) agonistic activity and having the chemical structure I:

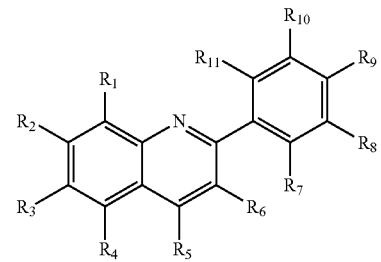

wherein:
(1) $R_1$, $R_2$, $R_3$, and $R_6$, are independently selected from the group consisting of
   (i) hydrogen (H), chlorine (Cl), fluorine (F), bromine (Br), iodine (I), cyano (CN), amino ($NH_2$), nitro ($NO_2$), alkoxy, haloalkyl, haloalkoxyl, substituted or unsubstituted alkyl, substituted or unsubstituted alkenyl, substituted or unsubstituted alkynyl, substituted or unsubstituted carbocycle, substituted or unsubstituted heterocycle, substituted or unsubstituted arene, substituted or unsubstituted heteroarene, SO$_3$H, an amide, thioamide, ester, thioester, a sulfonamide, a sulfinic acid, a sulfinamide, and (ii) SOR$_a$, and SO$_2$R$_b$, wherein R$_a$ and R$_b$ are each selected from H, substituted or unsubstituted alkyl, substituted or unsubstituted arene, and substituted or unsubstituted heteroarene;

(2) R$_7$, R$_8$, R$_9$, R$_{10}$, and R$_{11}$ are independently selected from the group consisting of (i), (ii), and (iii), wherein (iii) is a dioxolane formed from only one of the pairs R$_7$-R$_8$, R$_8$-R$_9$, R$_9$—R$_{10}$, and R$_{10}$-R$_{11}$; and (3) R$_4$ and R$_5$ are selected from the group consisting of (i), (ii), and (iv), wherein (iv) consists of carboxylic acid, hydroxamic acid, hydroxamic ester, phosphonic acid, phosphinic acid, sulfonic acid, sulfonamide, a sulfinic acid, acyl sulfonamide, sulfonylurea, acylurea, tetrazole, thiazolidine dione, oxazolidine dione, oxadiazol-5(4H)-one, thiadiazol-5(4H)-one, oxathiadiazole-2-oxide, oxadiazol-5(4H)-thione, isoxazole, tetramic acid, cyclopentane 1,3-diones, cyclopentane 1,2-diones, a squaric acid, a substituted phenol, heteroarene, amidine, hydroxyamide, alkyl hydroxyamidine, and salts of the above; and with the proviso that one of R$_4$ and R$_5$ is selected from (i) and (ii), and one of R$_4$ and R$_5$ is selected from (iv).

Clause 25. The ophthalmic composition of clause 24, wherein in the compound: R$_1$, R$_2$, R$_3$ and R$_4$ are H; R$_5$ is a carboxylic acid; R$_6$, R$_7$ and R$_{11}$ are H; and R$_8$ and R$_9$ are methoxy and R$_{10}$ is H, or R$_8$ is H and R$_9$ and R$_{10}$ are methoxy.

Clause 26. The ophthalmic composition of clause 24, wherein in the compound: R$_1$, R$_2$, R$_3$, R$_4$ R$_6$, R$_8$, R$_9$, and R$_{10}$ are are H; R$_5$ is a carboxylic acid; and R$_7$ and R$_{11}$ are selected from H and OH with the provisio that at least one of R$_7$ and R$_{11}$ is OH.

Clause 27. The ophthalmic composition of clause 24, wherein in the compound: R$_1$ is CH$_3$, R$_2$ is Cl, R$_5$ is a carboxylic acid group, and R$_3$, R$_4$, R$_6$, R$_7$, R$_8$, R$_9$, R$_{10}$, and R$_{11}$ are H.

Clause 28. The ophthalmic composition of clause 24, wherein in the compound: R$_1$ is H or alkyl; R$_2$ and R$_3$ are independently selected from H, Cl, F, Br, and I; one of R$_4$ and R$_5$ is carboxylic acid and one of R$_4$ and R$_5$ is H; R$_6$ is selected from H, Cl, F, Br, and I; and R$_7$, R$_8$, R$_9$, R$_{10}$, and R$_{11}$ are independently selected from H, Cl, F, Br, OH, and alkoxy.

Clause 29. The ophthalmic composition of clause 24, wherein in the compound: R$_1$, R$_2$ and R$_3$ are independently selected from H, Cl, F, Br, I, and alkyl; R$_4$ is H; R$_5$ is carboxylic acid; R$_6$ is selected from H, Cl, F, Br, and I; and R$_7$, R$_8$, R$_9$, R$_{10}$, and R$_{11}$ are independently selected from H, Cl, F, Br, OH, and alkoxy.

Clause 30. The ophthalmic composition of clause 24, wherein in the compound: R$_1$, R$_2$ and R$_3$ are independently selected from H, Cl, F, Br, and I; R$_4$ is H; R$_5$ is carboxylic acid; R$_6$ is selected from H, Cl, F, Br, and I; and R$_7$, R$_8$, R$_9$, R$_{10}$, and R$_{11}$ are independently selected from H, OH, and methoxy.

Clause 31. The ophthalmic composition of clause 24, wherein in the compound: R$_1$, R$_2$, R$_3$ and R$_4$ are H; R$_5$ is carboxylic acid; R$_6$ is H; and R$_7$, R$_8$, R$_9$, R$_{10}$, and R$_{11}$ are selected from H, OH, and methoxy, wherein at least one of R$_7$, R$_8$, R$_9$, R$_{10}$, and R$_{11}$ is OH.

Clause 32. The ophthalmic composition of clause 24, wherein in the compound: R$_1$, R$_2$, R$_3$ and R$_4$ are H; R$_5$ is carboxylic acid; R$_6$ is H; and R$_7$, R$_8$, R$_9$, R$_{10}$, and R$_{11}$ are selected from H and OH, wherein one of R$_7$ and R$_{11}$ is OH and one of R$_7$ and R$_{11}$ is H.

Clause 33. The ophthalmic composition of clause 24, wherein in the compound: R$_1$, R$_2$, R$_3$ and R$_4$ are H; R$_5$ is carboxylic acid; R$_6$ is H; and R$_7$, R$_8$, R$_9$, R$_{10}$, and R$_{11}$ are selected from H, OH, and methoxy, wherein at least one of R$_7$, R$_8$, R$_9$, R$_{10}$, and R$_{11}$ is methoxy.

Clause 34. The ophthalmic composition of clause 24, wherein in the compound: R$_1$, R$_2$, R$_3$ and R$_4$ are H; R$_5$ is carboxylic acid; R$_6$ is H; R$_7$ and R$_{11}$ are H; and R$_8$, R$_9$, and R$_{10}$ are selected from H and alkoxy, wherein at least one of R$_8$, R$_9$, and R$_{10}$ is an alkoxy.

Clause 35. The ophthalmic composition of any one of clauses 24-34 for use in a treatment of an ocular disorder or condition in a subject in need of such therapy, wherein the ocular disorder or condition is selected from the group consisting of retinal inflammation, retinal neovascularization, retinal vascular leakage, retinopathy of prematurity (ROP), diabetic retinopathy (DR), age-related macular degeneration (AMD), and diabetic macular edema (DME).

Clause 36. An ophthalmic composition comprising the phenylquinoline derivative compound of any one of clauses 24-34.

Clause 37. The ophthalmic composition of clause 36 for use in any one of method claims 1-23.

Clause 38. A kit, comprising the ophthalmic composition of any one of clauses 24-34, and instructions for use thereof in a treatment of an ocular disorder or condition in a subject in need of such therapy, wherein the ocular disorder or condition is selected from the group consisting of retinal inflammation, retinal neovascularization, retinal vascular leakage, retinopathy of prematurity (ROP), diabetic retinopathy (DR), age-related macular degeneration (AMD), and diabetic macular edema (DME).

Clause 39. A kit for use in any one of method claims 1-23, the kit comprising the phenylquinoline derivative compound of any one of clauses 24-34, and instructions for use thereof in the method.

While the present disclosure has been described herein in connection with certain embodiments so that aspects thereof may be more fully understood and appreciated, it is not intended that the present disclosure be limited to these particular embodiments. On the contrary, it is intended that all alternatives, modifications and equivalents are included within the scope of the present disclosure as defined herein. Thus the examples described above, which include particular embodiments, will serve to illustrate the practice of the inventive concepts of the present disclosure, it being understood that the particulars shown are by way of example and for purposes of illustrative discussion of particular embodiments only and are presented in the cause of providing what is believed to be the most useful and readily understood description of procedures as well as of the principles and conceptual aspects of the present disclosure. Changes may be made in the formulation of the various compositions described herein, the methods described herein or in the steps or the sequence of steps of the methods described herein without departing from the spirit and scope of the present disclosure. Further, while various embodiments of the present disclosure have been described in claims herein below, it is not intended that the present disclosure be limited to these particular claims. Applicants reserve the right to amend, add to, or replace the claims indicated herein below in subsequent patent applications.

What is claimed is:

1. A method of treating an ocular disorder or condition in a subject, comprising:
   administering to the subject a phenylquinoline derivative compound having peroxisome proliferator-activated receptor α (PPARα) agonistic activity, the compound having the chemical structure I:

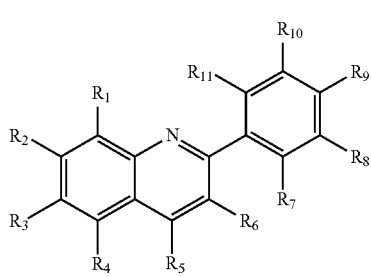

wherein:
   $R_1$ is $CH_3$, $R_2$ is selected from Cl, F, Br, and I, $R_5$ is a carboxylic acid group, and $R_3$, $R_4$, and $R_6$-$R_{11}$ are H; and
   wherein the ocular disorder or condition is selected from the group consisting of retinopathy of prematurity (ROP), diabetic retinopathy (DR), age-related macular degeneration (AMD), and diabetic macular edema (DME).

2. A method of treating an ocular disorder or condition in a subject, comprising:
   administering to the subject a phenylquinoline derivative compound having peroxisome proliferator-activated receptor α (PPARα) agonistic activity, the compound having the chemical structure I:

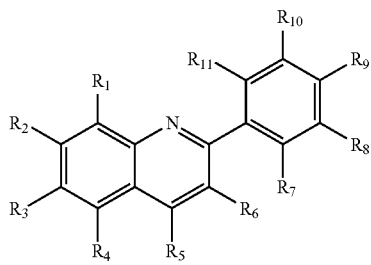

wherein:
   $R_1$ is $CH_3$, $R_2$ is Cl, $R_5$ is a carboxylic acid group, and $R_3$, $R_4$, and $R_6$-$R_{11}$ are H;
   and wherein the ocular disorder or condition is selected from the group consisting of retinopathy of prematurity (ROP), diabetic retinopathy (DR), age-related macular degeneration (AMD), and diabetic macular edema (DME).

3. A method of treating an ocular disorder or condition in a subject, comprising:
   administering to the subject a phenylquinoline derivative compound having peroxisome proliferator-activated receptor α (PPARα) agonistic activity, the compound having the chemical structure I:

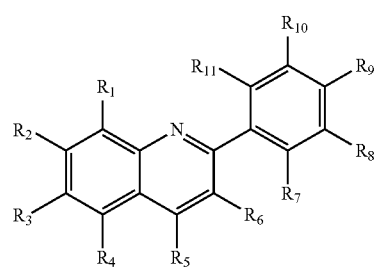

wherein:
   $R_1$ is $CH_3$, $R_2$ is F, $R_5$ is a carboxylic acid group, and $R_3$, $R_4$, and $R_6$-$R_{11}$ are H;
   and wherein the ocular disorder or condition is selected from the group consisting of retinopathy of prematurity (ROP), diabetic retinopathy (DR), age-related macular degeneration (AMD), and diabetic macular edema (DME).

4. The method of claim 1, wherein $R_2$ is Br.

5. The method of claim 1, wherein $R_2$ is Iodine (I).

* * * * *